United States Patent [19]

Simic et al.

[11] 4,045,506

[45] Aug. 30, 1977

[54] SEPARATION OF HYDROCARBON MIXTURES BY CATALYTIC DEALKYLATION

[75] Inventors: Milutin Simic, Novato; William A. Sweeney, Larkspur, both of Calif.

[73] Assignee: Chevron Research Company, San Francisco, Calif.

[21] Appl. No.: 672,703

[22] Filed: Apr. 1, 1976

[51] Int. Cl.² .......................... B01D 3/34; C07C 7/00
[52] U.S. Cl. ............................ 260/677 A; 203/29; 203/38; 203/65
[58] Field of Search .............. 203/38, 65, 28, 29; 260/677 A, 671 R, 672 R, 676 R

[56] References Cited

U.S. PATENT DOCUMENTS

| 3,121,754 | 2/1964 | Mattox et al. ................. 260/672 R |
| 3,159,567 | 12/1964 | Young .............................. 260/672 R |
| 3,751,509 | 8/1973 | Liakumovich et al. ........... 260/677 A |

FOREIGN PATENT DOCUMENTS

| 590,613 | 7/1947 | United Kingdom ............ 260/677 A |

*Primary Examiner*—Wilbur L. Bascomb, Jr.
*Attorney, Agent, or Firm*—D. A. Newell; John Stoner, Jr.; W. Keith Turner

[57] ABSTRACT

A process for separating mixtures of close boiling alkenes and alkanes which employs catalytic dealkylation of alkylphenols.

5 Claims, 1 Drawing Figure

CONTINUOUS PROCESS FOR SEPARATING HYDROCARBON MIXTURES

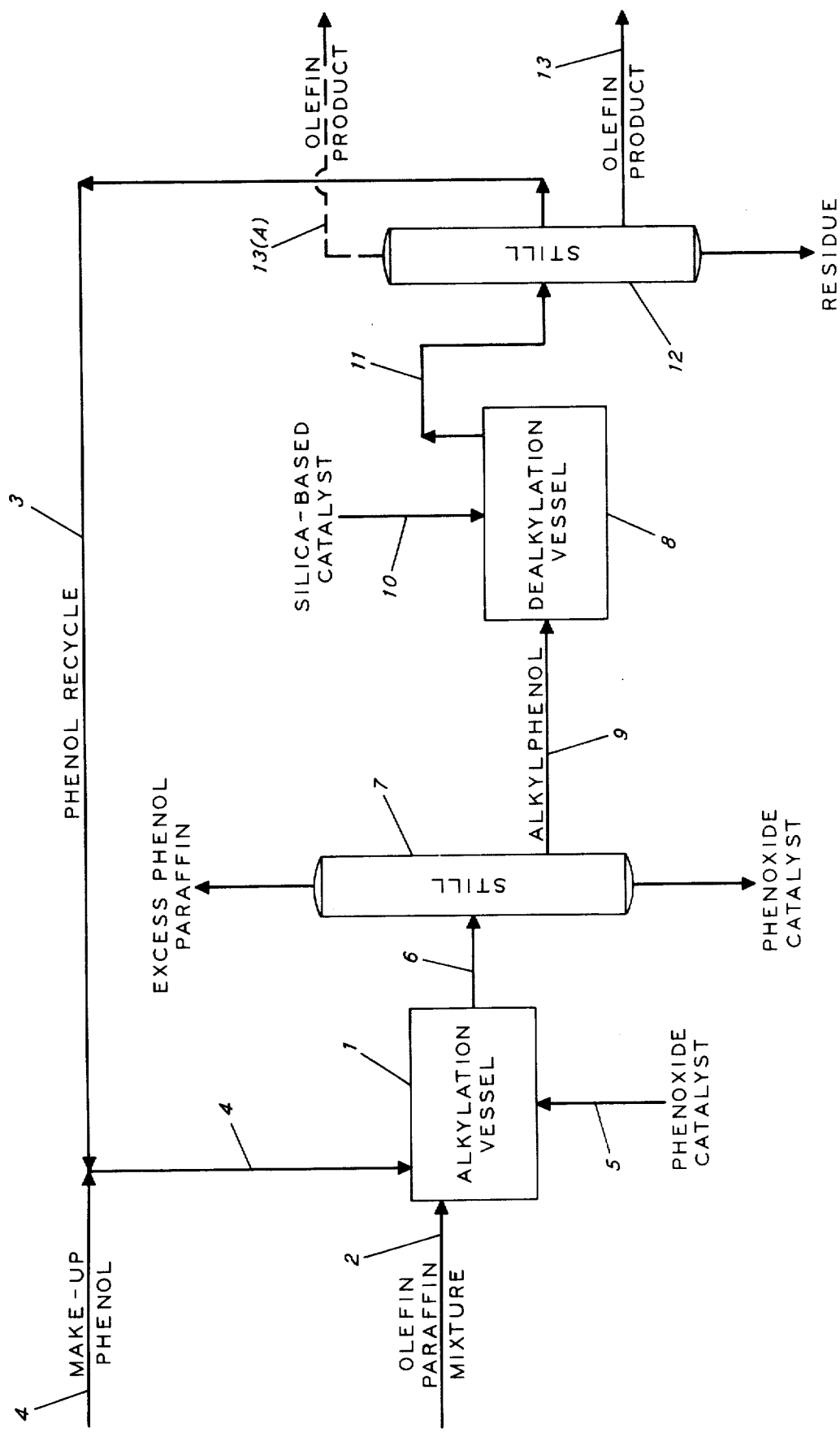

SEPARATION OF HYDROCARBON MIXTURES BY CATALYTIC DEALKYLATION

BACKGROUND OF THE INVENTION

The present invention relates to a process for separating mixtures of olefins and normal paraffins. In particular, the process of this invention employs phenoxide catalyzed olefin alkylation of phenols as a means of harboring olefins during paraffin separation, and catalytic cracking as a means of regenerating the olefins after separation.

A valuable application of the separation process of this invention lies in the area of biodegradable detergents.

High-boiling linear olefins containing at least about 8 carbon atoms are useful in the synthesis of biodegradable surfactants. While several processes are available for dehydrogenating normal paraffins to prepare linear olefins, these processes actually result in the formation of a mixture of paraffins and olefins. For example, U.S. Pat. No. 3,248,451, granted Apr. 26, 1966, describes the use of a cobalt molybdate compound supported on alumina to catalyze the vapor phase dehydrogenation of long-chain normal paraffins. Despite the improved yields reported, the product of the cobalt molybdate process contained significant amounts of paraffin.

While, in some cases, the paraffin-diluted olefins produced by dehydrogenation can be used as such; in many cases pure olefins are required. For instance, olefin sulfonation to prepare detergent compounds having particularly desirable biodegradability and efficacy employs pure olefins. As a consequence of the need for pure olefin feedstocks several processes have been suggested for separating mixtures of olefins and normal paraffins. The most notable of these separations employ molecular sieves or selective extraction. For instance, U.S. Pat. No. 3,767,724 granted Oct. 23, 1973, describes the use of extractive crystallization to separate acyclic hydrocarbon mixtures of alkenes and alkanes; U.S. Pat. No. 3,355,509 granted Nov. 28, 1967, and British Pat. No. 1,107,307 describe the separation of acyclic hydrocarbon mixtures by molecular sieves; and *Petroleum Processing*, August 1949, describes the use of cyclic adsorption to separate hydrocarbon mixtures. In many instances even these procedures do not successfully separate a 100% pure olefin fraction.

Accordingly, there is a continuing need for a process for separating mixtures of olefins and normal paraffins.

SUMMARY OF THE INVENTION

It has been found that close boiling mixtures comprising olefins and paraffins can be separated by a process comprising the steps of:

1. contacting a paraffin-diluted olefin mixture with a phenolic compound in the presence of an alkylation catalyst under conditions effective to cause olefin alkylation between the olefin and the phenol to prepare an alkylphenol;
2. recovering the alkylphenol;
3. heating the alkylphenol in the presence of a silica-based dealkylation catalyst under conditions effective to regenerate the olefin; and
4. rapidly separating the paraffin-free olefin from the reaction mixture.

In a preferred embodiment of the present process the paraffin-diluted olefin feedstock comprises substantially linear olefins.

BRIEF DESCRIPTION OF THE DRAWING

The several features of the present process will become more readily apparent from the following detailed description of the invention taken in conjunction with the accompanying drwing. The drawing illustrates a block-flow diagram of a preferred separation process employing olefin and alkylphenol recycle.

DETAILED DESCRIPTION OF THE INVENTION

The essential chemical reactions of the process of this invention are described by the following chemical equations

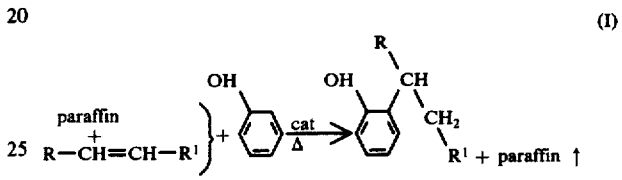
(I)

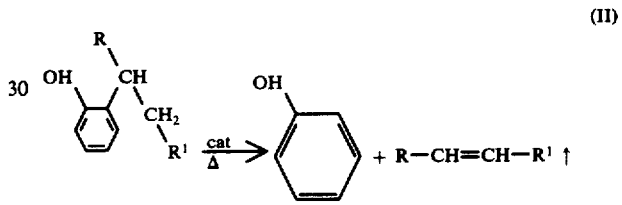
(II)

wherein $R-CH=CH-R^1$ is a high-molecular-weight olefin; and R and $R^1$ are hydrogen or alkyl.

The range of molecular weights of the olefin/paraffin mixtures suitable for use in the process of this invention is very wide. The process can be employed with olefin/paraffin mixtures comprising hydrocarbons having as few as 4 carbon atoms or as high as 40 carbon atoms and beyond. However, for practical purposes suitable feedstock mixtures will comprise olefins and paraffins having from about 8 to about 30 carbon atoms.

In the first step of the present process, a close-boiling mixture comprising paraffin-diluted olefins is contacted with a phenolic compound in the presence of an alkylation catalyst preferably a phenoxide catalyst under conditions effective to cause olefin alkylation between the phenol and the olefin.

As can be appreciated from Formula I, above, the olefin alkylation reaction employed in the first step of the present process serves as a means to harbor the high-molecular-weight olefin as an alkyl group. The olefin is subsequently regenerated by dealkylation in the third step of this process discussed in detail hereafter. Accordingly, the conditions of the alkylation reaction must be controlled to insure that the olefin is not destroyed or that side-reactions such as polymerization and disproportionation do not occur. For example, when substantially linear olefins are being separated for use in biodegradable surfactants the linear nature of the olefin must not be destroyed. It has been found that by employing select phenoxide catalysts described by the molecular structure

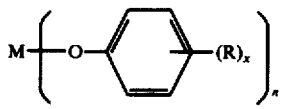

wherein M is aluminum or magnesium metal, $n$ is the valence of the metal, R is lower alkyl having from 1 to about 4 carbon atoms, and X is 0, 1 or 2, the side reactions of skeletal isomerization, polymerization, etc. will not occur: in particular, substantially linear olefins will be recovered as such. Hence phenoxide catalysts are preferred. The phenoxide catalyst will generally correspond to the phenolic compound being used to harbor the olefin during the separation since the metal moiety is free to exchange phenolic groups under the process conditions.

Phenoxide catalyzed alkylation is carried out under the usual liquid alkylation conditions, in particular, temperatures ranging from about 150° to about 320° C, preferably from about 220° to about 300° C. The reaction proceeds in the liquid phase so that sufficient pressure must be employed to maintain liquid conditions at the temperature of reaction. The ratio of phenolic compound to olefin on a molar basis ranges from about 1:1 to about 20:1, preferably from about 5:1 to about 15:1. At higher ratios less time is required for high conversion to alkyl phenol.

While phenol, per se, is of course a suitable phenolic reactant for use in the alkylation, it is also possible to employ alkylphenols. The phenolic compound must have an alkylatable position free or available by alkyl displacement to be useful in this process. It is preferable that this be a position ortho to the hydroxide group. It is believed advantageous to block the para position and one ortho position with a methyl group; i.e., by the use of 2,4-dimethyl phenol. Accordingly, phenolic compounds suitable for use in the process of this invention include, for example, phenol itself; o-, m-, and p-cresol; 2,4-dimethylphenol; alpha- or beta-naphthol; and the like. Phenol is preferred. When more than one phenolic alkylation position is available some of the product of the first step may contain more than one entering alkyl group. It has been found that the conditions of phenolic alkylation described above will similarly effect an alkyl displacement between the olefin and secondary or tertiary alkylphenol. This reaction is described by the reaction formula:

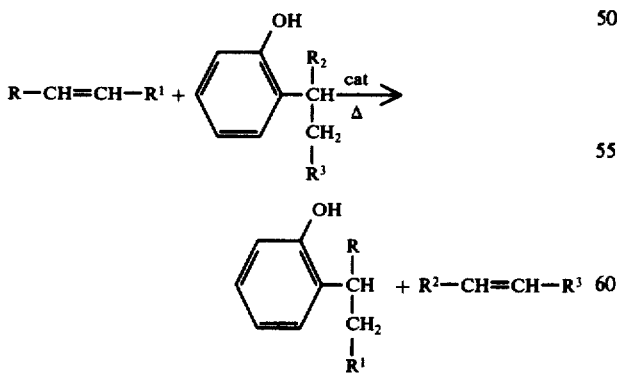

wherein R, R¹, R² and R³ are hydrogen or alkyl and R²—CH=CH—R³ contains at least two less carbon atoms than the lowest molecular weight R—CH=CH—R¹. Therefore, the phenolic compound employed in Step 1 may contain replaceable alkyl substituents which have at least 2 fewer carbon atoms that the olefin to be recovered.

In the second step of the present process the reaction product of the first step comprising paraffin, alkylphenol, excess phenol and unreacted olefin is heated under conditions sufficient to separate the reaction product into phenol, a paraffin-olefin mixture, and alkylphenol fractions. Separation can be achieved by employing conventional stripping and distillation techniques. For example, the excess phenol can be stripped off and paraffin-olefin mixture can be distilled overhead to leave alkylphenol as a bottoms product.

The above described second step, is necessarily somewhat modified when the phenolic compound contains a replaceable lower molecular weight alkyl group. Then the reaction product contains low molecular weight olefin in addition to the previously described components. Distillation separation then produces a low molecular weight olefin fraction, as excess phenol fraction, a paraffin-unreacted olefin fraction and an alkylphenol fraction. The low molecular weight olefin, and the phenol are by-products of this variation of the present process. The removal of low molecular weight olefin, e.g., by vaporization from the reaction zone during step 1 permits the reaction of alkylation by the higher molecular weight olefin to proceed to higher conversion. However, step 2 would still be required to separate the remaining components of the first reaction.

In the third step of the present process the recovered alkylphenol, which is now separated from the paraffins fraction of the initial olefin-paraffin mixture, is heated in the presence of a silica-based dealkylation catalyst under conditions effective to regenerate the olefin and phenol and to rapidly separate olefins from the dealkylation catalyst.

The reaction employed in the third step is a dealkylation reaction, illustrated by Equation II above, in which the alkyl group of the alkylphenol is removed to prepare phenol and to regenerate an olefin. Silica-based catalysts useful in the dealkylation reaction are well known in the art. In general, silica-based catalyst which contain an acidic oxide promoter, for example alumina or magnesia, are preferred. Silica-alumina catalysts are especially preferred. Accordingly, suitable silica-based dealkylation catalysts usually contain less than about 35%, preferably from about 5% to about 25% by weight of an acidic oxide promoter. These compositions are in a state of very slight hydration, and may contain small amounts of other material such as novolatile oxides.

Other suitable silica-based catalysts include aluminum silicates produced either from natural clay by activation or by purely synthetic methods. The activation of natural clays, mostly of the montmorillonite type, is carried out by treatment with dilute acids, which remove excess alumina and oxides of calcium, iron, etc., and thus enrich the silica content. Not only clays but also other aluminum silicates, such as molecular sieve zeolites, feldspar and the like when activated are suitable silica-based dealkylation catalysts.

The production of synthetic silica-based catalysts can be performed, for instance, by impregnating silica with aluminum salts; by direct combination of precipitated (or gelated) hydrated alumina and silica in appropriate proportions; or by joint precipitation of alumina and silica from an aqueous solution of aluminum and silicon salts. Synthetic silica-based catalysts may be produced by combination or hydrated silica with other hydrate bases as, for instance, magnesia or zirconia. The activated or calcined natural or synthetic catalysts must be relatively free of impurities such as alkaline salts and ferric oxide. The presence of such impurities causes sintering of the catalyst surface on regeneration and a consequent drop in catalytic activity.

During the above described dealkylation reaction rapid separation of olefinic product and process control of conversion and temperature are critical. It has been found that by controlling these variable the silica-based dealkylation catalysts may be employed to catalyze dealkylation without undersirable side reactions, such as skeletal isomerization, polymerization and disproportionation. More particularly, it has been found that at moderately high conversions of from about 70% to about 80%, based on product weight, and temperatures below about 300° C and with separation of the olefin as it is formed, the regenerated olefin is essentially consistent with the initial feedstock olefin; whereas, at higher conversions, higher temperatures, or excess contact time with the catalyst, the product will contain significant amounts of skeletally isomerized olefin and increasing amounts of polymeric material. Obviously control over isomerization is particularly important where linear olefins are the desired product. Dealkylation starts at about 250° C. To maintain a steady dealkylation rate, it has been found preferable to gradually increase temperature to about 300° C.

As a final step the regenerated olefin is recovered from the reaction product of the third step comprising olefin and phenol. Preferably this step is carried out simultaneously with the third step, i.e., the reaction is carried out in a vessel having a vapor removal means and as the olefin is formed it is vaporized from the reaction mixture. The phenolic compound may or may not vaporize at the same time. To aid in olefin removal an inert gas stream may be passed through the reaction mass. Suitable gases include nitrogen, high temperature steam, and the like. Conventional or vacuum distillation may be employed to recover olefin as an overhead product. In the second and fourth steps distillation is described as the preferred physical method for separation. Other physical methods of separation such as extraction or adsorption are also contemplated but with minimum olefin-catalyst contact time.

The present process is particularly advantageous where continuous processing is employed. In particular, it is possible to recycle phenolic compounds tht do not have replaceable alkyl groups. The drawing is a block-flow diagram illustrating a preferred continuous process employing phenol recycle. Referring to the drawing, vessels 1 and 8 are reaction vessels containing a heating means, a temperature control means, and a means for mixing. Fresh feedstock comprising a mixture of olefins and paraffins of essentially the same olecular weight in line 2 is continuously fed into reactor 1. At the same time recycled phenol in line 3 is combined with make-up phenol in line 4, and then continuously charged to vessel 1. Phenoxide catalyst is charged to vessel 1 through line 5. Vessel 1 is maintained within the process limits discussed above. The crude reaction product comprising alkylphenol, exces phenol, unreacted olefin and paraffin is continuously removed from vessel 1 through line 6, and passed into still 7. Still 7 is operated under conditions sufficient to vaporize the paraffin diluent which is recovered as a by-product and is useful as a flow to a dehydrogenation process. The intermediate fraction from still 7 comprising alkylphenol is continuously removed and passed through line 9 to vessel 8. The bottoms from still 7 contain the phenoxide catalyst and other high boiling substances. Silica-based catalyst is charged to vessel 8 through line 10. Vessel 8 is maintained within the process limits discussed above. Vaporied crude reaction product comprising phenol and linear olefins is continuously removed from vessel 8 through line 11, and passed into still 12. Still 12 is operated under conditions sufficient to recover olefins which are continuously removed from still 12 through line 13 when the olefins have a boiling point greater than that of phenol. When the olefin boiling point is lower than that of phenol, recovery is via line 13A. If the Phenol and olefin have the same boiling point, they are removed through the same line and washed with water to separate. The phenol is then dehydrated before recycled. Phenol is continuously removed from still 12 through line 3 and combined with make-up phenol in line 4.

In accordance with the drawing, the present invention emcompasses a continuous process for separating olefins from mixtures of olefins and paraffins comprising the steps of: (1) contacting a paraffin-diluted olefin with a phenol in the presence of a phenoxide alkylation catalyst in a first reaction zone under conditions effective to cause olefin alkylation of the phenol to prepare a reaction product comprising paraffin and alkylphenols: (2) separating paraffins from the reactor product of step (1); (3) heating the alkylphenol residue of step (2) in the presence of a silica-based dealkylation catalyst in a second reaction zone under conditions effective to prepare a reaction product comprising olefin, and phenol; (4) separating phenol from the reaction product of step (3); (5) recovering a paraffin-free olefin; (6) recycling phenol from step (4) to the first reaction zone of step (1).

EXAMPLES

EXAMPLES 1-6: Separation of $nC_{1a}-C_{2n}$ Olefin/Paraffin Mixture

In the following examples a mixture of olefins and paraffins containing from 18 to 20 carbon atoms was separated using the process of this invention.

The mixture comprised about 10% olefins, and was prepared by dehydrogenation of $nC_{18}-C_{20}$ paraffins. Typical dehydrogenation conditions are described in U.S. Pat. No. 3,531,543.

In accordance with the process of this invention, phenol alkylation of the $C_{18}-C_{20}$ olefin-paraffin mixture was conducted using an aluminum phenoxide catalyst prepared by heating a reaction vessel containing 18 grams of aluminum metal and 3,180 grams of phenol to about 140° C at about 25 psig for about 1 hour to form the phenoxide. The reaction vessel was then vented to release hydrogen formed during the reaction. About 8,160 g of the olefin-paraffin mixture was then added to the reaction vessel. The temperature was increased to 290° C and held for 8 hours. After cooling to 170° C, 72 grams of water was added and the resulting mixture was held at 170° C for 1 hour to destroy the aluminum phenoxide catalyst. The resulting monoalkyl phenol was recovered by distillation.

Six aliquots of the $C_{18}-C_{20}$ monoalkyl phenol (Examples 1-6) were heated in the presence of a silica-alumina dealkylation catalyst. The catalyst which was employed is a commercially available silica-based composition manufactured by Mobil under the descriptive name "TCC Beads." More particularly, the catalyst comprised 90% by weight, $SiO_2$ and 10% $Al_2O_3$; has a bulk density of 48.6–51.2 lbs/ft³; a surface area of 333–345 m²/g; a pore volume of 0.361 - 0.375 cc/g; a particle density of 1.21–1.29 g/cc; and a metal content of: 0.09–0.12%, by weight of sodium, 0.005–0.018% of iron and less than 0.002 of chromium. Prior to use, the beads were crushed and screened to a size between 32 and 100 mesh. This is the catalyst used in examples 5 and 6. The catalyst for examples 1 through 4 was treated as follows: 20 grams of the 32 to 100 mesh particles was mixed with 0.25 grams of sodium hydroxide dissolved in 25 ml of water and after being held for 1 hour at room temperature it was dried at 150° C for 3 hours. The reactions were run batchwise using two types of equipment. In one, a stirred reaction flask was connected directly to a condenser; and the dealkylation product removed using a nitrogen stream. In the second, the stirred flask was equipped with a 5 inches Vigreux column; and the product removal was vacuum-assisted.

The products of dealkylation were analyzed by gas chromatography methods. The material balance analysis was done in a 10 foot column packed with methylphenyl silicone rubber (OV-17) on a chromasorb W (diatomaceous earth) support. The isomer distribution analysis was carried out on a 300 foot capillary column coated with a a silicone oil (SF—96, manufacture by General Electric Co.). The conditions and results of each run are summarized in Table I, below.

EXAMPLE 7-10: Dealkylation of Monoalkylphenol Made From $nC_{19}$ Randomly Isomerized Olefin Following the procedure of Examples 1-6, the dealkylation step of the present process was examined using monoalkylphenol prepared by phenol alkylation of randomly isomerized $nC_{19}$ olefins. Four runs (Examples 7-10) was examined; the conditions and results are summarized in Table II, below.

TABLE II

DEALKYLATION OF n-$C_{19}$ LINEAR ALKYLPHENOL[1] OVER SILICA-ALUMINA CATALYSTS

| | | CONDITIONS | | | CONVERSION | PRODUCT OLEFIN | |
|---|---|---|---|---|---|---|---|
| EXAMPLE | CATALYST | TIME, HRS. | TEMP, °C | PRODUCT REMOVAL[6] | LAP DEALKYLATED % | LINEAR % | BRANCHED % |
| 7 | TCC[3] + 1.25% NaOH | 7.5 | 260–300 | $N_2$ | 78 | 100 | — |
| 8 | " | 8[5] | 270–310 | $N_2$ | 72 | 100 | — |
| 9 | TCC | 3.5 | 270–315 | $N_2$ | 83 | 58 | 42 |
| 10 | Durabead-1[4] (untempered) | 3 | 260–315 | $N_2$ | 85 | 75 | 25 |

[1]Linear $C_{19}$ alkylphenol made with randomly isomerized $C_{19}$ olefin
[2]Fifty parts LAP + 1.5 parts catalyst
[3]90% $SiO_2$ and 10% $Al_2O_3$
[4]90% $SiO_2$, 10% $Al_2O_3$ having a density of 74–82g/cc, a pore volume of 0.35 cc/g and a surface area of 250 m²
[5]Run at $N_2$ flow of 150 ml/min for 3 hrs, 350 ml/min for 3 hrs, and 500 ml/min for 2 hrs
[6]Assisted With $N_2$ (500 ml/min)

In the case of $C_{18}$–$C_{20}$ linear alkylphenol, lower-molecular-weight LAP is dealkylated as a faster rate than the higher-molecular-weight LAP. In most cases, linear olefin was produced almost exclusively at up to 70–80% LAP conversion. Branching occurred at higher temperatures. To maintain steady dealkylation it was necessary to gradually increase the temperature to 300° C and over.

What is claimed is:

1. A process for separating a close-boiling mixture comprising substantially linear olefins and paraffins which comprises the steps of:
   1. contacting a paraffin-dilute substantially linear olefin mixture with a phenolic compound in the presence of an aluminum or magnesium phenoxide alkylation catalyst under conditions effective to cause olefin alkylation between the olefin and the phenol to prepare alkylphenols;
   2. recovering the alkylphenols;
   3. heating the alkylphenols in the presence of a silica-based dealkylation catalyst at a temperature below about 300° C under conditions effective to regenerate the olefin at conversions of from about 70–80% by weight; and
   4. rapidly separating the parafffin-free olefin.
2. A process according to claim 1 wherein said mixture comprises $C_8$ to $C_{30}$ olefins.
3. A process according to claim 1 wherein said phenoxide alkylation catalyst is an aluminum triphenoxide.
4. A process according to claim 1 wherein said dealkylation catalyst is a silica-alumina catalyst.
5. A continuous process for separating a close-boiling mixture comprising substantially linear olefins and paraffins which comprises the steps of:
   1. contacting a paraffin-diluted substantially linear olefin with a phenolic compound in the presence of an aluminum or magnesium phenoxide alkylation catalyst in a first reaction zone under conditions

TABLE I

DEALKYLATION OF LINEAR ALKYLPHENOL OVER SILICA-ALUMINA CATALYTS[1]

| | | CONDITIONS | | | CONVERSION | PRODUCT OLEFIN | |
|---|---|---|---|---|---|---|---|
| EXAMPLE | CATALYST | TIME, HRS. | TEMP, °C | PRODUCT REMOVAL[3] | LAP DEALKYLATED % | LINEAR % | BRANCHED % |
| 1 | TCC[2] + 1.25% NaOH | 2.5 | 280–360 | $N_2$ | 90 | 90 | 10 |
| 2 | " | 3 | 280–360 | $N_2$ | 65 | 86 | 14 |
| 3 | " | 1.5 | 250 | $N_2$ | 56 | 98 | 2 |
| 4 | " | 10 | 280–340 | Vacuum | 98 | 84 | 16 |
| 5 | TCC | 8 | 250–310 | Vacuum | 96 | 86 | 14 |
| 6 | TCC | 2 | 270–300 | $N_2$ | 54 | 98 | 2 |

[1]Fifty parts LAP + 1.5 parts catalyst
[2]90% $SiO_2$ and 10% $Al_2O_3$
[3]Assisted with $N_2$ (500 ml/min) or vacuum (150–200 mm Hg)

effective to cause alkylation of phenol to prepare a reaction product comprising paraffin and alkylphenols;
2. recovering the alkylphenols;
3. heating the alkylphenols in the presence of a silica-based dealkylation catalyst in a second reaction zone at a temperature below about 300° C under conditions effective to cause dealkylation of the alkylphenol to prepare a reaction product comprising olefin, and phenol at a conversion of from about 70–80% by weight;
4. recovering paraffin-free substantially linear olefin;
5. recycling phenol from step (3) to the first reaction zone of step (1).

* * * * *